US00PP09182P

United States Patent [19]

Dehan

[11] Patent Number: Plant 9,182

[45] Date of Patent: Jun. 27, 1995

[54] IMPATIENS PLANT NAMED 'VENUS'

[75] Inventor: Klara Dehan, Holon, Israel

[73] Assignee: Danziger "Dan" Flower Farm, Hashiva, Israel

[21] Appl. No.: 299,612

[22] Filed: Sep. 2, 1994

[51] Int. Cl.[6] ..... A01H 5/00

[52] U.S. Cl. ..... Plt./87.6

[58] Field of Search ..... Plt. 87.6

*Primary Examiner*—James R. Feyrer

*Attorney, Agent, or Firm*—Foley & Lardner

[57] ABSTRACT

A new and distinct cultivar of Impatiens plant named Venus, characterized by its bicolor flowers comprised mainly of light purple with dark red-purple spots, medium size flowers, compact growth habit, excellent branching, dark green leaves infused with purple, and its floriferous habit.

1 Drawing Sheet

The present invention relates to a new and distinctive cultivar of Impatiens plant, botanically known as Impatiens, commerically known as New Guinea impatiens, and known by the cultivar name Venus.

The new cultivar was developed by the inventor Klara Dehan in Mishmar Hashiva, Israel in a controlled breeding program. The female or seed parent was a cultivar identified by the breeding number BR-1048, and the male or pollen parent was a cultivar identified by the breeding number DC-4124. Both parents are proprietary cultivars used in the breeding program. The new cultivar was selected by the inventor from the progeny of the stated cross.

Asexual reproduction of the new cultivar by leaf cuttings performed by the inventor in Mishmar Hashiva, Israel has established that the unique features of this new impatiens are stabilized and are reproduced true to type in successive propagations.

The following characteristics in combination distinguish the new Impatiens Venus from both its parent varieties and other cultivated Impatiens of this type known and used in the floriculture industry:

1. Medium size flowers.
2. Flowers are bicolored. The main color is light purple, with dark red-purple spots.
3. Compact, growth habit.
4. Excellent branching.
5. Dark green leaves, infused with purple. Leaves are relatively small.
6. Very floriferous habit.

The accompanying color photographic drawing illustrates the overall appearance of the cultivar, with the colors being as true as it is reasonably possible to obtain in a colored reproduction of this type.

The following is a detailed description of the new Impatiens cultivar based on plants produced under commercial practice in Mishmar Hashiva, Israel. The plants described were grown in a net-covered greenhouse during the summer season with temperatures ranging from 35° C. maximum to 18° C. minimum. Color references are made to The Royal Horticultural Society Colour chart except where general terms of ordinary dictionary significance are used.

Parentage: The female parent BR-1048 and the male parent DC-4124 are seedlings from breeding program.

Propagation:

*Type cutting.*—Leaf cuttings.

*Time to initiate roots.*—7–8 days at 25° C. summer; 8–9 days at 20° C. winter.

*Rooting habit.*—Roots well.

Plant description:

*Form.*—Excellent self-branching produces a full, rounded symmetrical plant.

*Habit of growth.*—Compact growth habit.

*Foliage.*—Size: Relatively small, mature leaves 7.0 cm long and 3.0 cm wide. Shape: Lanceolate to ovate. Margin: Serrated. Color: Young and mature foliage, top side 147A infused with purple; under side 187A; Venation: Purple.

Flowering description:

*Flowering habits.*—The initiation of flower buds takes about 5–6 weeks from potting leaf cutting. Flower completely opens approximately 9 weeks after potting.

*Natural flowering season.*—The new cultivar flowers under ambient conditions in Israel all year, but in its winter season with less light, there are fewer flowers.

*Flower buds.*—Buds before opening are approximately 1.5 cm in length and 1.0 cm in width. Length of spur is 3 cm and color is light green; pedicel is light green and 4.5 cm in length.

*Flowers borne.*—Flowers are carried on strong stems and are fully open from initiation in about 2 weeks; flowering continues all season.

*Quantity of flowers.*—Very floriferous, with approximately 25 flowers being open at the same time.

*Petals.*—Shape: Two (2) pairs of heart-shaped petals, each pair being light purple, and a single larger dark red-purple petal; petals overlap. Color: Top side, main color 77D with color of spots and larger petal 74A; no noticeable fading; under side main color 77C with spots of 67B and 60C; Number of petals: Five (5). Size of flowers: Medium, about 5 cm in diameter.

*Reproductive organs.*—Stamens: One (1) in number. Anthers: Round, white color. Pollen color: White. Pistils: Stigma: Round in shape, purple in color. Ovaries: Four (4) in number, 1 mm in size; light green in color.

Disease resistance: No significant disease problem noted to date.

I claim:

1. A new and distinct cultivar of Impatiens plant named Venus, as illustrated and described.

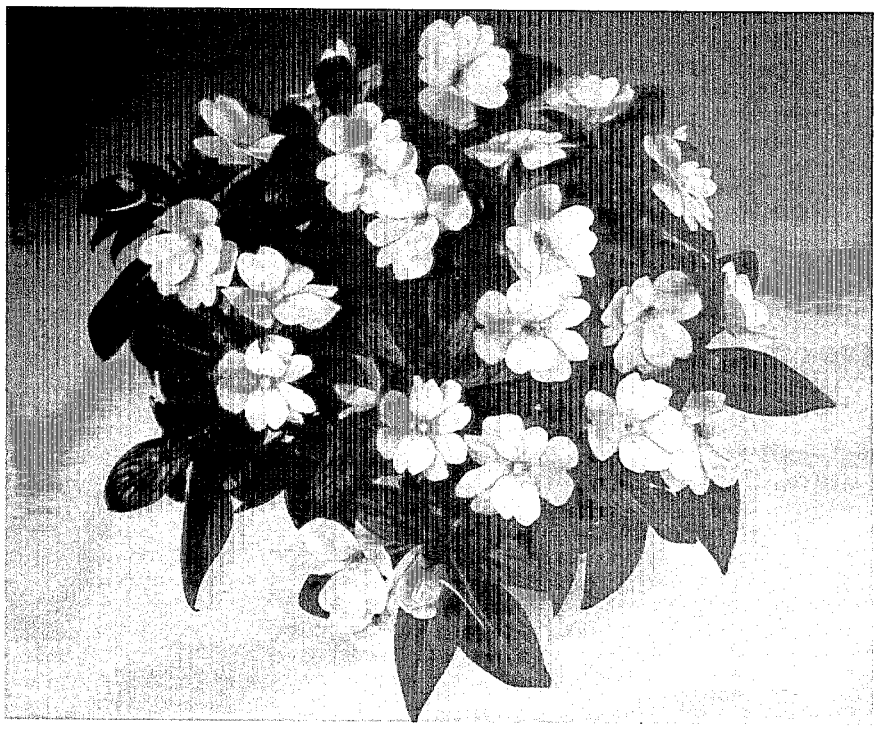

* * * * *